(12) United States Patent  (10) Patent No.: US 9,265,850 B2
Davis et al.  (45) Date of Patent: Feb. 23, 2016

(54) ULTRAVIOLET SANITIZER WITH WAND

(71) Applicant: GreenZapr, Inc., Indianapolis, IN (US)

(72) Inventors: Michael E. Davis, Indianapolis, IN (US); Steve Redmond, Brownsburg, IN (US)

(73) Assignee: GreenZapr, Inc., Indianapolis, IN (US)

( * ) Notice: Subject to any disclaimer, the term of this patent is extended or adjusted under 35 U.S.C. 154(b) by 0 days.

(21) Appl. No.: 14/202,142

(22) Filed: Mar. 10, 2014

(65) Prior Publication Data

US 2014/0264084 A1 Sep. 18, 2014

Related U.S. Application Data

(60) Provisional application No. 61/779,192, filed on Mar. 13, 2013.

(51) Int. Cl.
*A61L 2/10* (2006.01)

(52) U.S. Cl.
CPC .............. *A61L 2/10* (2013.01); *A61L 2202/15* (2013.01); *A61L 2202/16* (2013.01); *A61L 2202/24* (2013.01)

(58) Field of Classification Search
CPC ... A61L 2/10; A61L 2202/16; A61L 2202/24; A61L 2202/15
USPC ......... 250/455.11, 504 R, 504 H; 607/93, 94, 607/98; 422/24
See application file for complete search history.

(56) References Cited

U.S. PATENT DOCUMENTS

| | | | | |
|---|---|---|---|---|
| 4,287,554 A * | 9/1981 | Wolff | .................... | A61N 5/0614 250/504 R |
| 4,820,015 A * | 4/1989 | Mogi | .................... | G02B 6/0008 385/115 |
| 5,902,552 A | 5/1999 | Brickley | | |
| 5,968,445 A | 10/1999 | McCarville et al. | | |
| 6,272,768 B1 | 8/2001 | Danese | | |
| 6,571,049 B1 * | 5/2003 | Nath | ........................ | A61C 1/08 250/504 H |
| 6,709,128 B2 * | 3/2004 | Gordon | ................ | A61C 19/004 250/504 H |
| 7,459,694 B2 | 12/2008 | Scheir et al. | | |
| 7,626,187 B2 | 12/2009 | Younts | | |
| 7,703,262 B2 * | 4/2010 | Till | ........................ | B65B 55/08 250/455.11 |
| 7,834,328 B2 | 11/2010 | Redmond et al. | | |
| 8,109,981 B2 * | 2/2012 | Gertner | ................ | A61N 5/0603 606/13 |

(Continued)

FOREIGN PATENT DOCUMENTS

EP  0 277 505  8/1988
JP  2002-085348  3/2002

OTHER PUBLICATIONS http://www.americanultraviolet.com/uv-curing-solutions/spot-curing-spectrum-100.cfml American Ultraviolet, 212 S. Mt. Zion Road, Lebanon, IN 46052—Admitted Prior Art, Mar. 2014.

(Continued)

*Primary Examiner* — Wyatt Stoffa
(74) *Attorney, Agent, or Firm* — Woodard, Emhardt, Moriarty, McNett & Henry LLP

(57) ABSTRACT

An ultraviolet sanitizer with flexible wand. A flexible wand is connected to a generator of ultraviolet radiation. The generator is mounted within a housing and connectable to a source of electrical energy. The distal wand end includes a switch for controlling the emission of the ultraviolet radiation from the wand with a distal tip directing the radiation toward the surface to be sanitized.

19 Claims, 15 Drawing Sheets

(56) References Cited

U.S. PATENT DOCUMENTS

| | | | |
|---|---|---|---|
| 8,226,887 B2 | 7/2012 | Harmon et al. | |
| 8,415,647 B2* | 4/2013 | Hartung | 250/455.11 |
| 8,431,075 B2 | 4/2013 | Davis | |
| 2002/0063954 A1* | 5/2002 | Horton, III | A61L 2/10 359/350 |
| 2004/0204747 A1* | 10/2004 | Kemeny | A61N 5/0603 607/94 |
| 2005/0107853 A1* | 5/2005 | Krespi | A61B 18/18 607/89 |
| 2005/0165462 A1* | 7/2005 | Bays | A61B 18/24 607/88 |
| 2005/0177208 A1* | 8/2005 | Irwin | A61N 5/0603 607/94 |
| 2005/0254237 A1* | 11/2005 | Nath | F21L 4/00 362/190 |
| 2006/0085052 A1* | 4/2006 | Feuerstein | A46B 15/0002 607/90 |
| 2006/0155349 A1* | 7/2006 | Kemeny | A61N 5/0603 607/94 |
| 2006/0212099 A1* | 9/2006 | Riddell | A61N 5/0601 607/88 |
| 2006/0217789 A1* | 9/2006 | Perez | A61N 5/0616 607/94 |
| 2006/0228251 A1* | 10/2006 | Schneberger | A61L 2/0011 422/23 |
| 2006/0235492 A1* | 10/2006 | Kemeny | A61N 5/0603 607/88 |
| 2007/0219600 A1* | 9/2007 | Gertner | A61N 5/0603 607/88 |
| 2008/0077199 A1* | 3/2008 | Shefi | A61N 5/0613 607/88 |
| 2008/0131337 A1 | 6/2008 | Lucas et al. | |
| 2008/0159908 A1* | 7/2008 | Redmond | A61L 2/10 422/24 |
| 2008/0177357 A1* | 7/2008 | Perez | A61N 5/0603 607/91 |
| 2009/0184267 A1* | 7/2009 | Bar | F26B 3/28 250/504 R |
| 2009/0248004 A1* | 10/2009 | Altshuler | A61B 18/18 606/33 |
| 2010/0222852 A1* | 9/2010 | Vasily | A61N 5/0603 607/89 |
| 2010/0274328 A1* | 10/2010 | Morgan | A61N 5/06 607/88 |
| 2011/0309032 A1* | 12/2011 | Makl | A61L 2/10 210/748.1 |
| 2011/0317959 A1* | 12/2011 | Ohta | G02B 6/4214 385/38 |
| 2013/0018442 A1* | 1/2013 | Irwin | A61N 5/0603 607/94 |

OTHER PUBLICATIONS www.newport.com/Liquid-Light-Gjuides/378731/1033/info.aspx—Newport's Model 76840—76843—Liquid Light Guide, 79 in., 220-600nm, 0.2 in. Core, 043.Na—1996-2014 Newport Corporation, 150 Longbeach Road, Stratford, CT 06615—Admitted Prior Art, Mar. 2014.

* cited by examiner

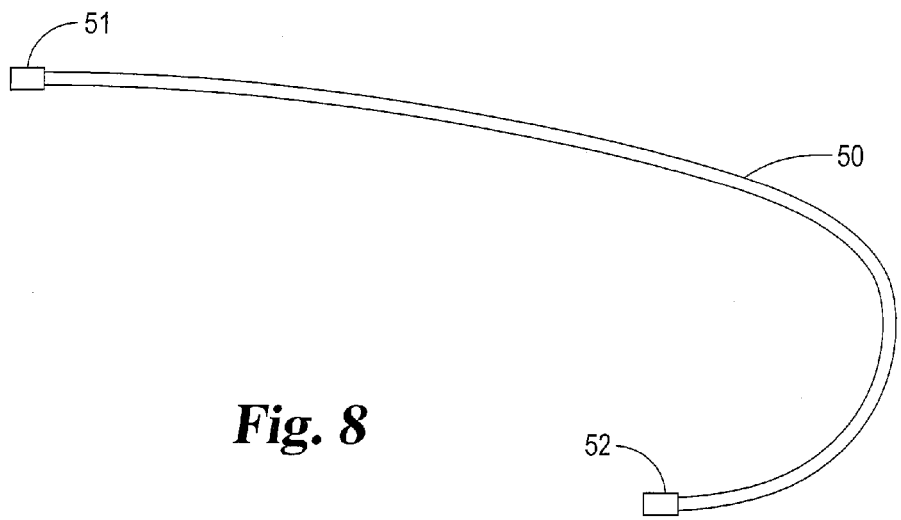
Fig. 8
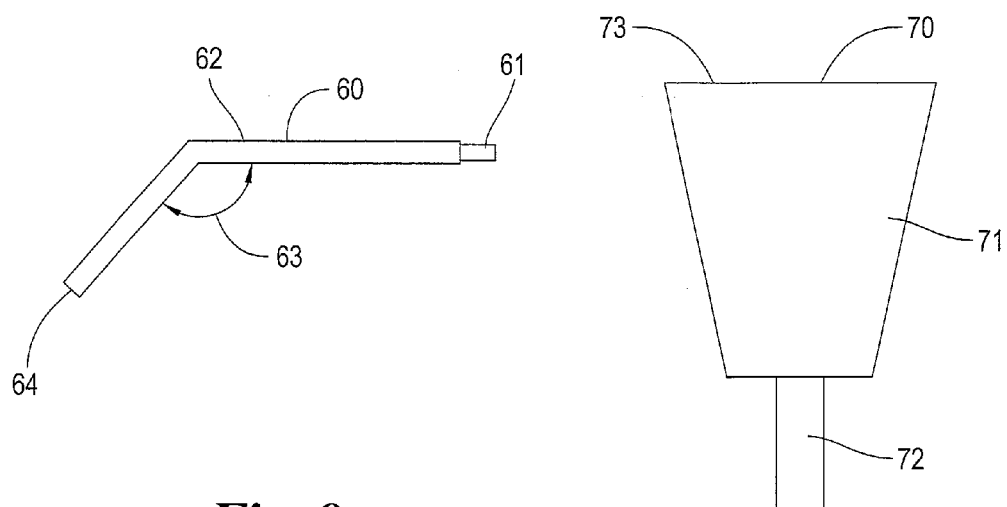
Fig. 9
Fig. 10

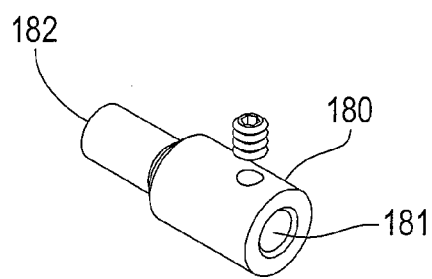
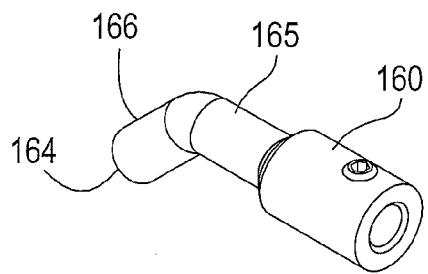
*Fig. 16*        *Fig. 17*
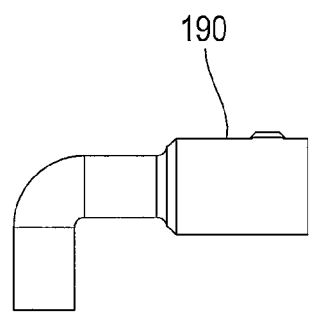
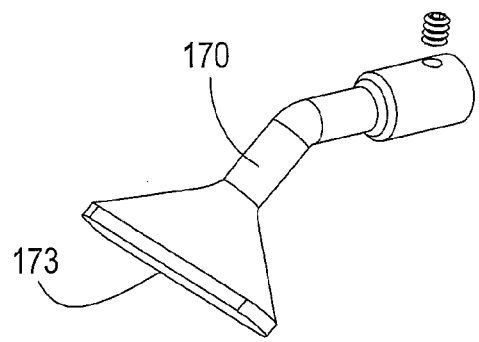
*Fig. 18*        *Fig. 19*

ULTRAVIOLET SANITIZER WITH WAND

BACKGROUND OF THE INVENTION

1. Field of the Invention

The present invention relates generally to the field of apparatus and methods for sterilizing various surfaces.

2. Description of the Prior Art

In U.S. Pat. No. 8,431,075 there is described a method and apparatus for destroying infectious material present on a field used for various activities including sports. A vehicle is moved across the field and includes downwardly shining ultraviolet lamps that expose the synthetic grass blades to ultraviolet radiation. Prior to the exposure, brushes are used to contact the blades and position the blades so that they extend upwardly towards the light. As the vehicle quickly moves across the field, the infectious material is destroyed thereby providing a more efficient result without spraying the field with chemicals as used in the prior sterilization methods.

Heretofore, ultraviolet radiation has been used to destroy infectious materials present within various medical facilities, such as, surgery rooms. Thus, it is known to destroy infectious material using ultraviolet radiation.

While the generation of ultraviolet, type C (UVC) radiation for the purpose of sterilization of surfaces is not a new idea, the traditional handheld products on the market can only disinfect easy accessible areas. Left are unsterilized surfaces that are in gaps, cracks, crevasses, corners, inside tubing, pipes and boxed in areas. Disclosed herein is a method and device to direct a narrowly focused high powered beam of UVC radiation through a flexible tube. The distal end of the tube is then placed into the ordinarily unreachable areas that are to be disinfected causing the UVC radiation to eradicate genus, etc.

Various approaches have been used in decontaminating surfaces through the use of ultraviolet light. For example, in U.S. Pat. No. 7,459,694, there is disclosed a mobile germicidal system for decontaminating walls and a ceiling of a room. Germicidal lamps are positioned adjacent the wall and/or ceiling to thereby sterilize the surface. U.S. Pat. No. 5,902,552 discloses an ultraviolet air sterilization device for connection to an air handling duct for the purpose of sterilizing the air as it flows through the duct. U.S. Pat. No. 5,968,445 discloses a wheeled carriage with a handle to allow the operator to move the sterilization device over a floor.

An apparatus using ultraviolet light is disclosed in U.S. Pat. No. 6,272,768 for treating an object. A handheld device for moving across a surface to eradicate undesirable elements thereon is disclosed in U.S. Pat. No. 7,626,187. U.S. Pat. No. 8,226,887 discloses a mobile disinfectant device and method using ultraviolet light to sterilize a surface. A UV spot curing system for hardening epoxy material using a wand emitting ultraviolet light is available from American Ultraviolet under Model Spectrum 100.

SUMMARY OF THE INVENTION

One embodiment of the present invention is an ultraviolet sanitizer with a wand comprises a main housing and an electrical power supply. A fan is mounted to the main housing and connected to the power supply operable to interiorly cool the housing. A generator is connected to the power supply operable to generate ultraviolet radiation and the generator has an ultraviolet radiation emitting outlet. A flexible wand has a main body to transmit ultraviolet radiation. The wand has a proximal end connected to the ultraviolet radiation emitting outlet of the generator to receive the ultraviolet radiation and further has a distal end to direct the ultraviolet radiation against the surface to be sanitized.

Another embodiment of the present invention is a flexible wand directs radiation from a source of radiation toward a surface for sanitation thereof and comprises a flexible main body to transmit radiation from a source of radiation toward a surface for sanitation of the surface. The main body has a wand proximal end connectable to the source of radiation to receive the radiation therefrom and a wand distal end to direct the radiation against a surface to be sanitized. A tip is mounted to the wand distal end to direct the radiation from the wand against a surface to be sanitized.

An object of the present invention is to provide a flexible wand to dispense UVC radiation against surfaces to be sanitized.

It is an object of the present invention to provide a handheld wand that may be swiped across a hard to reach area to destroy infectious material thereon.

A further object of the present invention is to provide a convenient and portable ultraviolet sanitizer that dispenses radiation via a flexible wand toward the surface to be sanitized.

A further object of the present invention is to provide a mobile apparatus that is used direct a narrow focus UVC radiation beam towards unsterilized surfaces in gaps, cracks, crevasses, corners, inside tubing, pipes and boxed in areas.

Related objects and advantages of the present invention will be apparent from the following description.

BRIEF DESCRIPTION OF THE DRAWINGS

FIG. 8 is a view of the radiation wand;

FIG. 9 is an enlarged side view of a 5 mm tip mounted to the distal end of the wand of FIG. 8; and FIG. 10 is an enlarged side view of a broad tip mountable to the distal end of the radiation wand of FIG. 8.

FIG. 16 is an enlarged perspective view of the straight tip mountable to the distal end of the wand of FIG. 14.

FIG. 17 is an enlarged perspective view of an angled tip mountable to the distal end of the wand of FIG. 14.

FIG. 18 is an enlarged side view of a right angle tip mountable to the distal end of the wand of FIG. 14.

FIG. 19 is an enlarged perspective view of a spreader or fan tip mountable to the distal end of the wand of FIG. 14.

DESCRIPTION OF THE PREFERRED EMBODIMENTS

Figure 1:
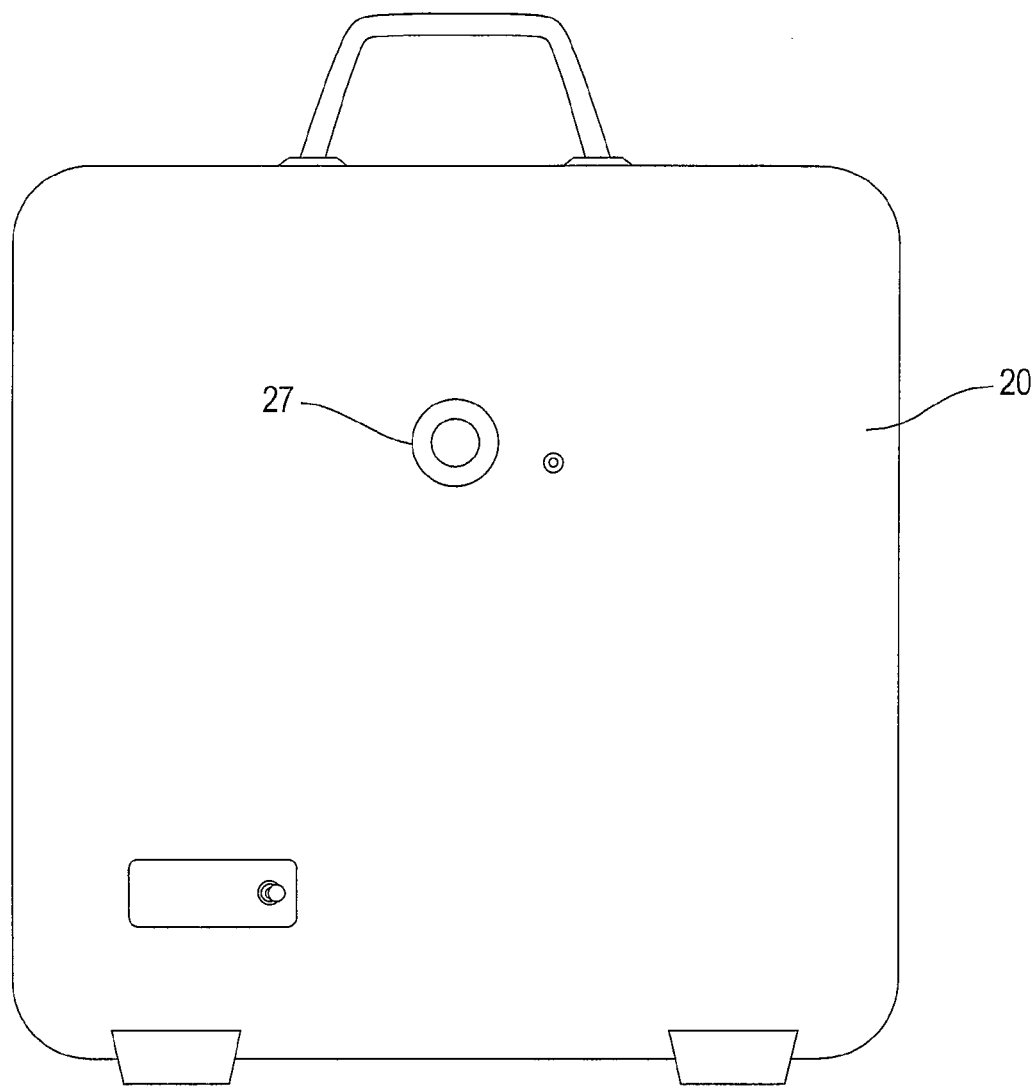
FIG. 1 is a front view of the alternate embodiment of a portable device for emitting UVC radiation.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The ultraviolet sanitizer 20 (FIG. 1) includes a enclosure made from metal, such as 12 gauge aluminum sheet, forming a generally rectangular or square interior to house the main components of the sanitizer. While the enclosure may take a variety of shapes, in one embodiment, sanitizer 20 consists of two halves mechanically fastened along a vertical seam. The enclosure houses an internal power supply 21 (FIG. 4), an arc lamp 22, a parabolic reflector 23, a shutter 24, a culminator 25, and a wavelength filter 26. The outlet 27 is mounted to the enclosure and provides a means for the focused radiation to be directed outwardly of the sanitizer. A housing fan 28 is mounted to the enclosure to remove heat generated by the arc lamp. The sanitizer shown in FIGS. 1-10 illustrates the alternate embodiment of the sanitizer assembly, whereas the preferred embodiment of the sanitizer is illustrated in the remaining figures starting with FIG. 11.

The light source is a CW arc lamp model 7515 or equal and is operable to generate ultraviolet radiation, type C having a wave length of approximately 100 to 290 nanometers. The lamp is a short arc mercury vapor bulb contained in a separate enclosure within the outer enclosure to ensure against UVC light leakage. The lamp enclosure 30 (FIG. 5) may be produced from a variety of metallic materials. For example, a 12 gauge aluminum sheet may be used to form a generally square or rectangular enclosure. Inside interior box 30 is mounted the arc lamp 22 in front of the parabolic reflector 23 which focuses the energy produced by the lamp into an aluminum cylinder 31 (FIG. 5) mounted in front of the lamp 22 and contained within interior box 30. A variety of parabolic reflectors may be utilized such as available from Edmunds Optical.

The metal cylinder 31 dissipates heat generated from the lamp 22 and cooperates together with fan 28 (FIG. 4) to dissipate heat from the sanitizer thereby increasing the life thereof. Further, the cylinder serves as a mechanism for holding an infrared wave length filter 26 (FIG. 6), such as available from Edmunds Electronics. The filter is operable to remove infrared light, typically extending from the nominal red edge of the visible spectrum at 0.74 micrometers to 0.3 mm. In addition, cylinder 31 holds in place the culminator 25 that is located on the opposite sides of the wavelength filter 26. The culminator focuses the radiation into a narrow beam which then exits via outlet 27. Arc lamp 22 is operable to generate not only ultraviolet, type C radiation but other wavelengths. The parabolic reflector 23 concentrates the radiation emitted by the lamp to pass into cylinder 31 wherein the filter is operable to eliminate some frequencies other than the UVC radiation and focuses the radiation in a narrow beam via the culminator 25 eventually exiting interior enclosure 30 and the sanitizer 20 into the flexible wand 50 (FIG. 3) directed against the surface to be sanitized.

Figure 5:
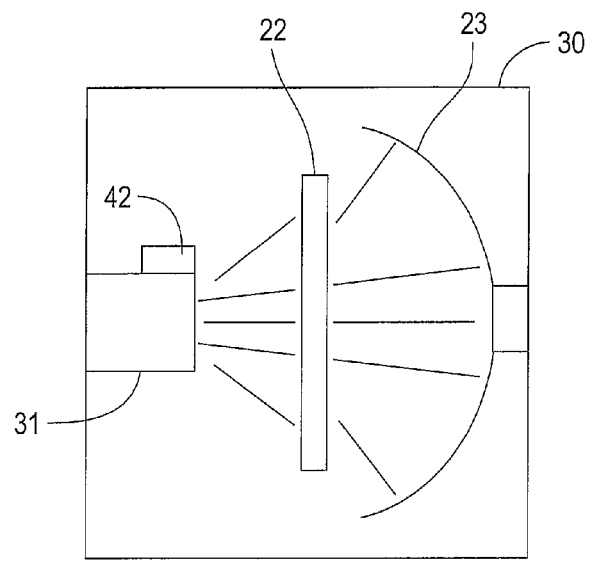
FIG. 5 is a diagram illustrating the radiation emitter within the device of FIG. 1 and located in front of a parabolic reflector directing the radiation beam into a filter.
Figure 6:
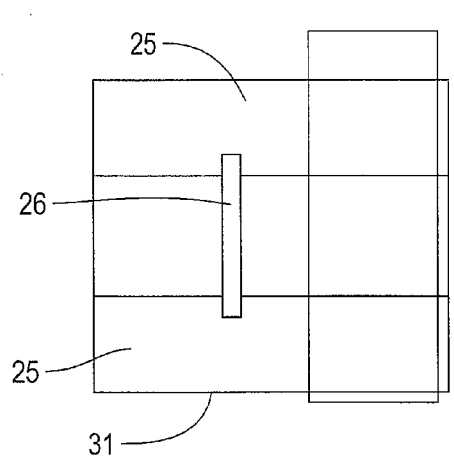
FIG. 6 is a sketch of a cylinder holding the wave length filter, and shutter.

Cylinder 31 includes a passage 40 (FIG. 7) through which the UVC radiation is directed. A shutter 24 is slidably mounted to cylinder 31. The shutter may be produced from a carbon steel material and is movable by an electromagnet 42 (FIG. 5). The magnet is operable to move the shutter to block passage 40 preventing the UVC beam from moving through passage 40 and is also operable to move the shutter apart from the passage to allow the beam to pass through the passage and eventually to the wand. An on/off switch may be provided on sanitizer 20 and/or the distal end portion of the wand to allow the operator to turn on and off the system thereby controllably directing the amount of UVC radiation against the surface to be sanitized. Various alternatives may be provided for construction of the operation of the shutter. In one embodiment, deactivation of the magnet allows the shutter 24 (FIG. 7) to drop into the cylinder thereby blocking passage 40 whereas with the electromagnet energized, the shutter is withdrawn apart from the passage 40.

Light guide 50 (FIG. 8) is operable to guide the UVC radiation from outlet 27 (FIG. 4) whereat the wand proximal end 51 is mounted. The light guide is available from Lumatec under Series 250 and includes an aqueous solution of $NaH_2PO_4$ contained within a fluorocarbon polymer flexible tube sealed at the ends with quartz plugs to contain the fluid and transmit light at the desired light wave lengths of 220 to 280 nanometers. A light guide may be used such as Oriel Instruments DUV series or Newport's Model 76840. The length of the flexible light guide should be not shorter than 39.4" to accommodate easy application of the UVC light.

Figure 7:
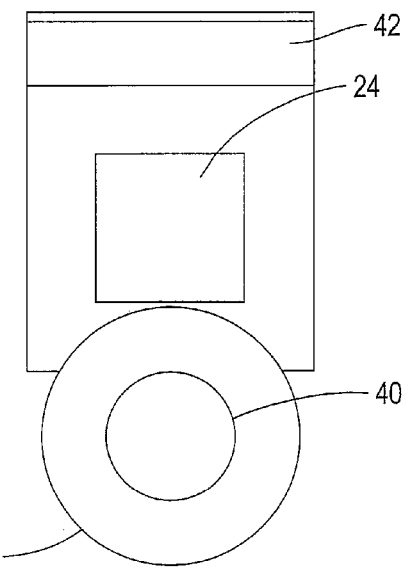
FIG. 7 is an enlarged end view of the cylinder of FIG. 6.

At the distal end of the light guide is a switch, push button or otherwise, activated by the users thumb to control the position of shutter 24 thereby allowing or disallowing light to be directed through passage 40 (FIG. 7). The switch and the wires to the switch are fixed to the light guide via shrink tubing and are encased with cross-woven protective nylon fabric along the entire length of the guide being secured to each end with shrink tubing. The proximal end 51 of the light guide plugs into the exit 27 of the aluminum cylinder 31 as well as the wires from the push button switch that utilize a 3 mm plug into the face of the outer enclosure of the sanitizer.

At least two interchangeable tips 60 (FIG. 9) and 70 (FIG. 10) may be selected to help direct UVC light to the area to be sanitized more effectively and ergonomically depending on the application. The proximal end 61 of tip 60 plugs into the distal end 52 of light guide 50 with the main body 62 of the tip being generally cylindrical in configuration with the proximal end portion of the tip arranged at an obtuse angle 63 thereby allowing the tip distal end 64 to be conveniently positioned adjacent the area to be sanitized. The diameter of the main body 62 is 5 mm. Tip 60 may be produced from aluminum tubing approximately four inches long with obtuse angle 63 being approximately 150 degrees. Variations in tip 60 are included in the present invention. For example, angle 63 may be 135 degrees or any angle that facilitates the positioning of the distal end portion. Likewise, the diameter of the main body 62 may be less than or greater than 5 mm. In one embodiment, the main body 71 (FIG. 10) of tip 70 broadens out to a distal end 73 of approximately 6 inches whereas the mounting end portion of main body 71 may be 154 mm.

Advantages of the present invention will be apparent from the above description. For example, the device is portable being lightweight and relatively small in size. The device and method have a dual purpose in that broad surfaces as well as narrow areas may be sanitized. The remote shutter operation provides for not only safety but also control of the amount of radiation to be applied to the surface. In one embodiment, the device has a high power input thereby providing a fast and effective treatment with the range of power output being variable between 3.5 watts to 6000 micro watts. The supplied radiation is 3.5 watts at the tip with a frequency of 254 nm.

The broad tip 70 has a truncated main body 71 with the proximal end 72 extending into the distal end 52 of light guide 50. The opposite end 73 of main body 71 has a large diameter thereby allowing the emitted radiation to be spread over a larger area as compared to tip 60. Tip 70 is particularly useful in sanitizing large flat areas.

The method of use of sanitizing a surface with the device disclosed herein includes various steps. First, the power supply 21 (FIG. 4) is connected via power cord 80 to a suitable source of current. The distal end of the wand is grasped and positioned at one end of the surface to be treated. The user applies the UVC dosing by activating the thumb switch moving the shutter 24 (FIG. 7) apart from passage 40. The tip of the wand is moved in one direction in a swiping motion at approximately 10 centimeters per second at a right angle to the gap containing the contaminated material. The motion of the wand tip is then reversed pulling the wand back with the same swiping motion while turning the light guide to a 45 degree angle to the left or right of the surface to be treated. The wand can then be moved in a swiping motion in the opposite direction at an angle to the surface to be treated at 135 degrees. This method can ensure the UVC flowing from the tip of the wand will produce different angles of incidence upon the target surface thereby reflecting UVC light to all areas of the treatable area.

Another method to treat a mold area inside a wall or cabinet is to first open an insertion point large enough for the guide to enter. The guide is then inserted through the opening to abate the mold infested blind or hidden areas. Using time and dosage calculations suitable for the application, the guide is then moved in a fashion that illuminates the hidden area with adequate UVC saturation to achieve mold abatement. Use of an optical viewing fiber in conjunction with the sanitizer to see into the blind areas may be useful in certain situations.

The larger wand tip 70 may be used for flat surfaces such as counters, tables or work areas. Using a waving motion within 2 centimeters of the contaminated surface at an approximate motion of 10 centimeters per second is useful. The tip can also be in contact with the surface area using the same method and speed. Some of the various components for the sanitizer are commercially available. For example, the bulb within the arc lamp may be obtained from Sylvania Osram under Model HBO 50 W AC L1 with the electromagnet being obtained from AWP. Various switches and power cords are available from a variety of sources. A power supply 21 for powering the various components of sanitizer 20, such as CW Arc mdl 7515 from Hello trade is suitable.

Figure 11:
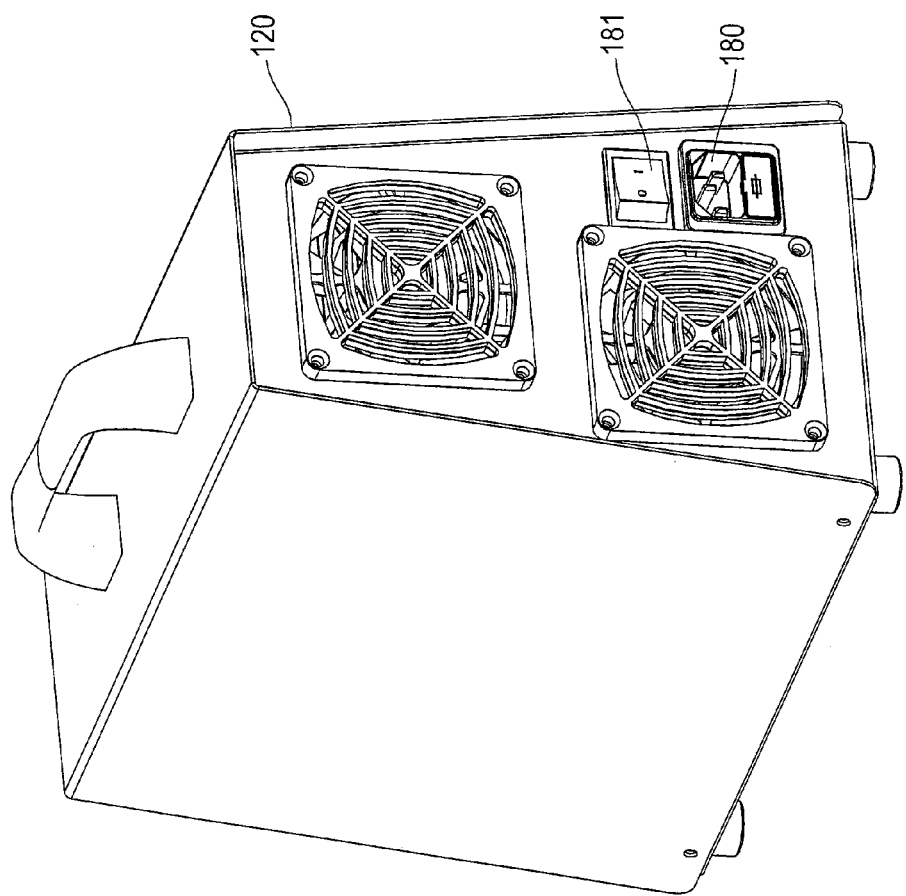
FIG. 11 is a rear perspective view of the preferred embodiment of the portable device for emitting UVC radiation.
Figure 12:
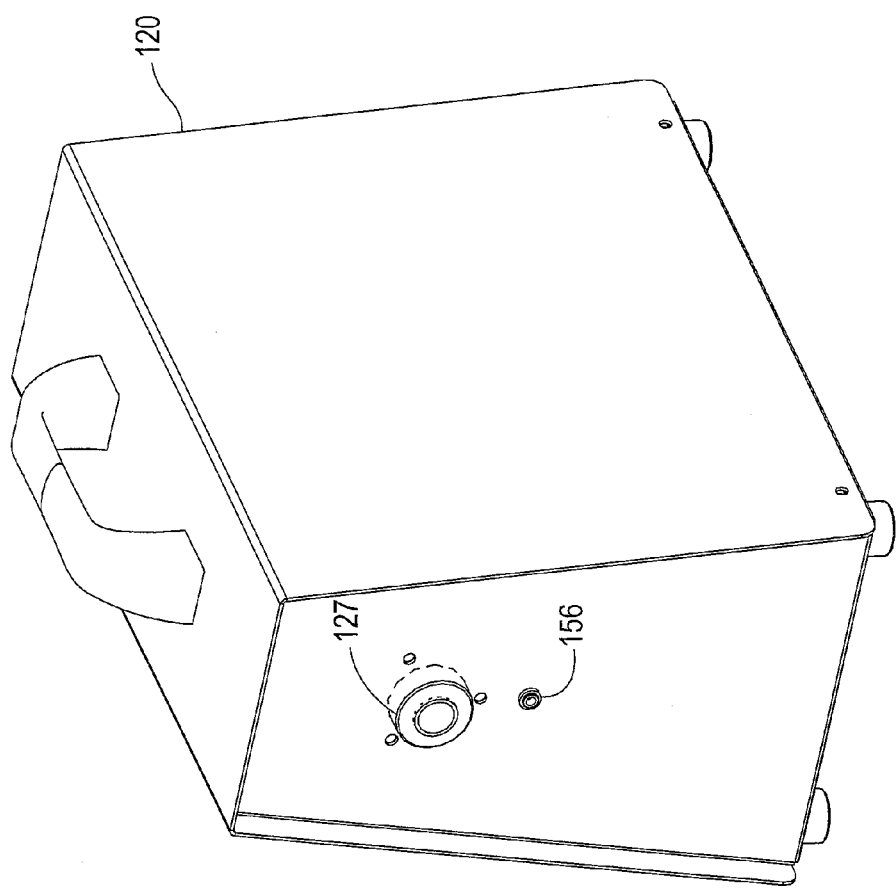
FIG. 12 is a front perspective view of the device of FIG. 11.
Figure 14:
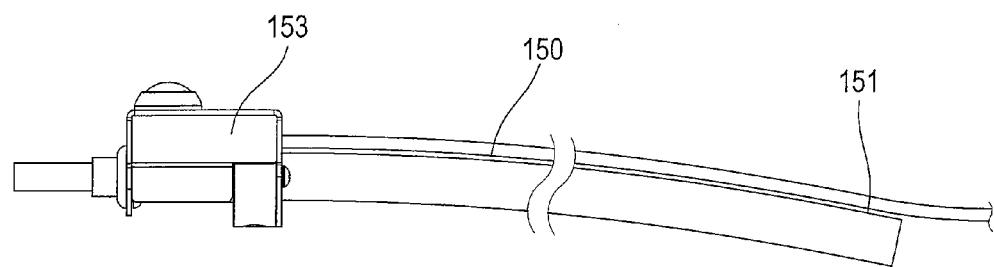
FIG. 14 is a fragmentary side view of the wand mountable to the device of FIG. 11.

The preferred embodiment of the sanitizer shown in FIGS. 11 and 12. Sanitizer 120 includes a conventional metal enclosure with a handle provided to allow the sanitizer to be carried. The sanitizer includes a power cord 180 extendable from the sanitizer housing to a suitable source of electrical energy for powering the internal power supply and the lamp within the housing thereby generating the ultraviolet radiation emittable from the flexible wand 150 (FIG. 14) having its proximal end 151 connected to the outlet 127 (FIG. 12). A conventional manual on/off switch 181 (FIG. 11) is provided at the rear of the housing to connect or disconnect the source of electrical energy to the internal components of the sanitizer.

Figure 2:
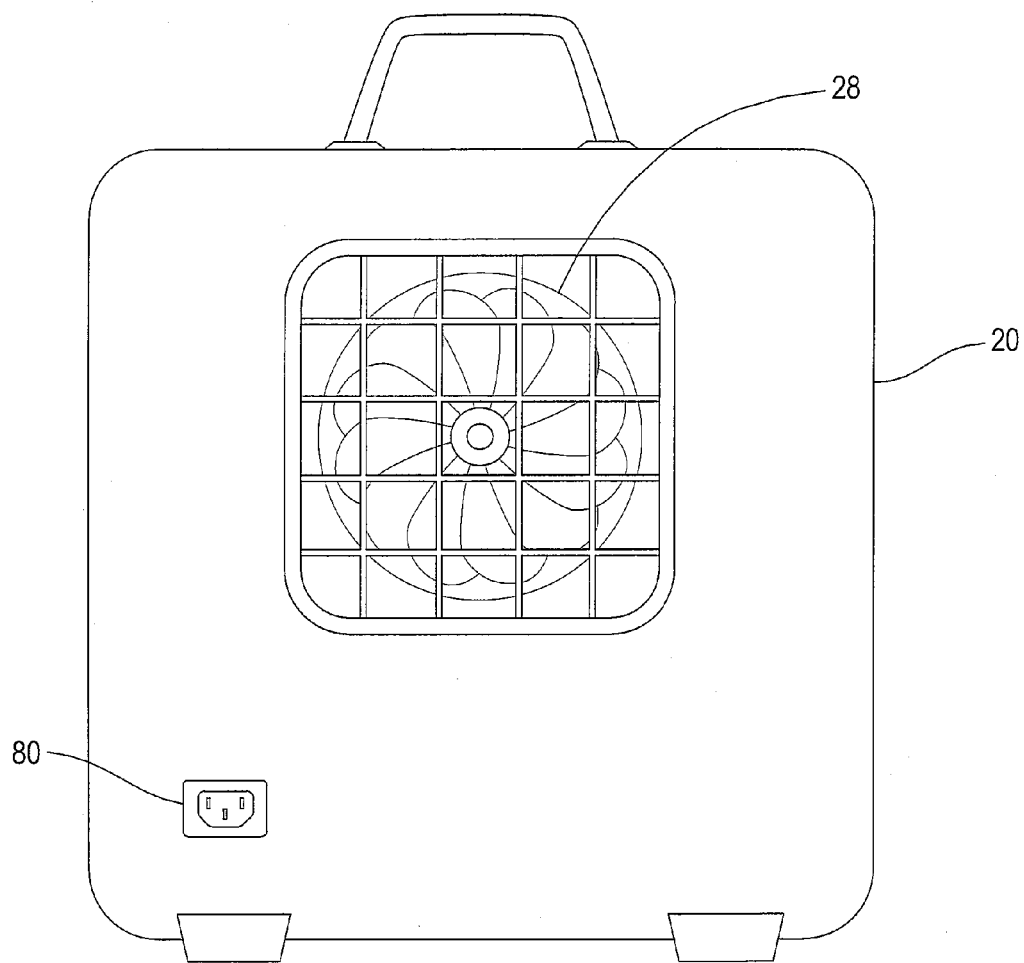
FIG. 2 is a rear view of the device of FIG. 1.
Figure 3:
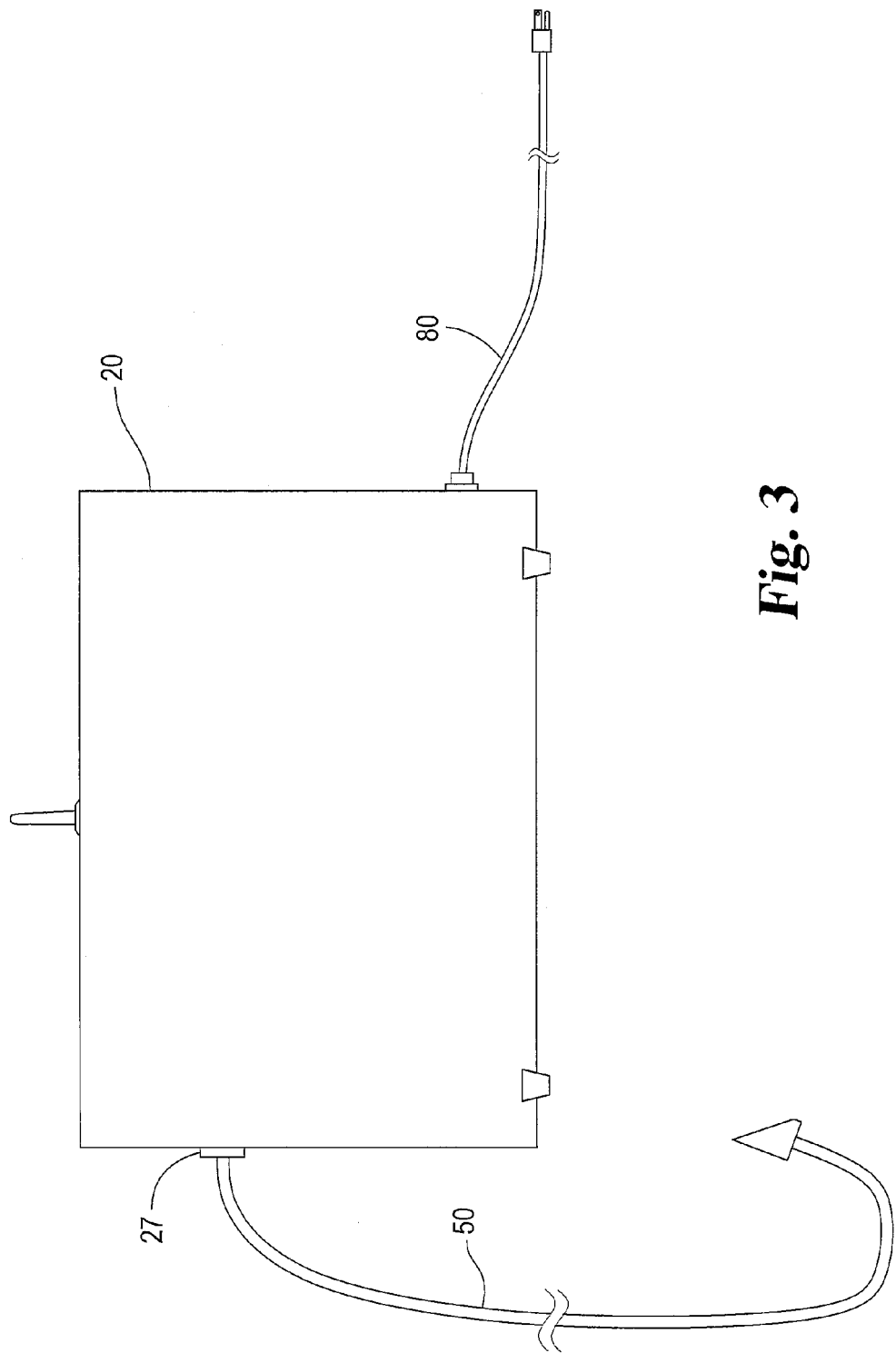
FIG. 3 is a right side view of the device of FIG. 1.
Figure 4:
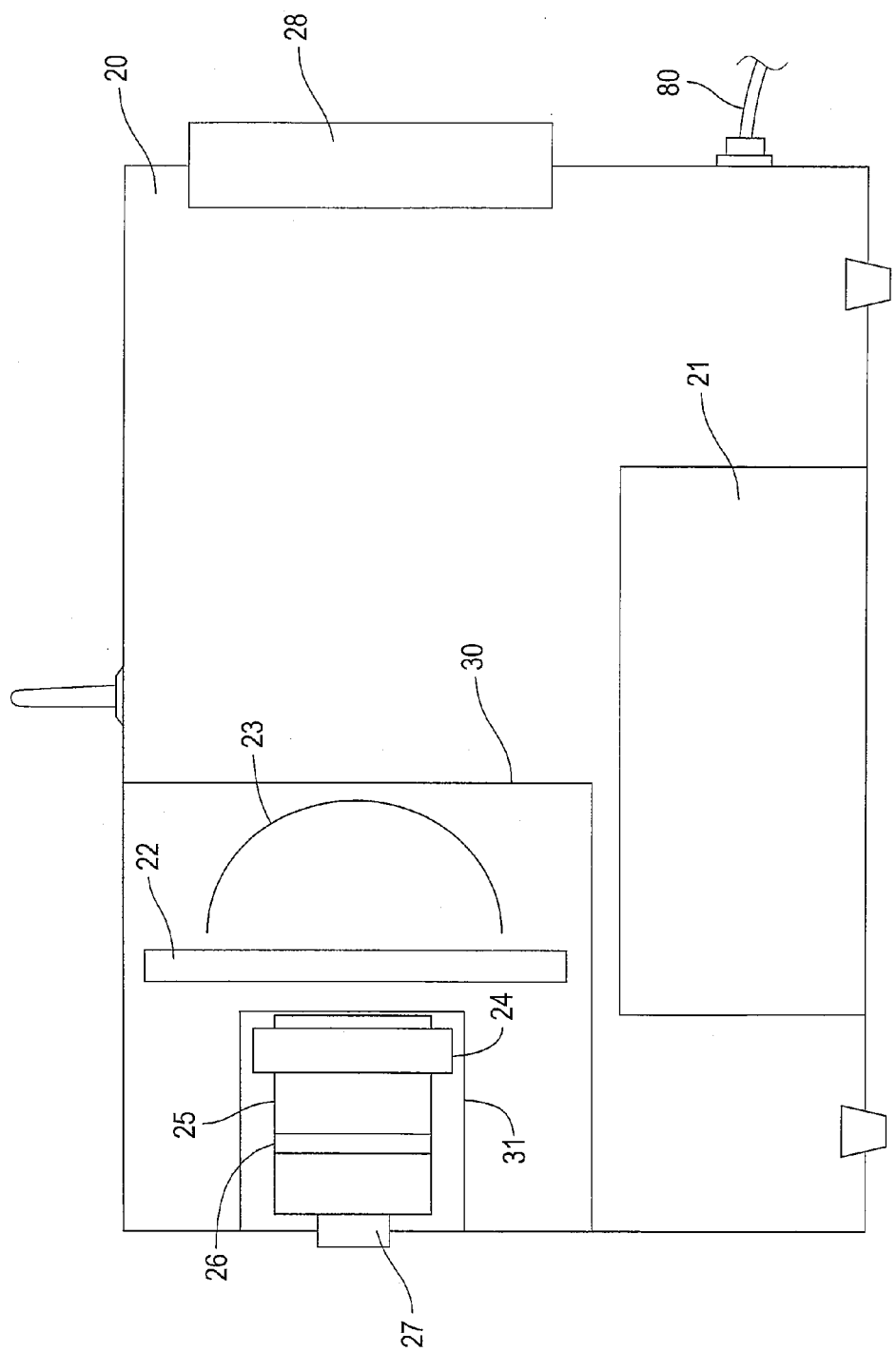
FIG. 4 is an internal diagram depicting various components within the device of FIG. 1.

Whereas the alternate embodiment shown in FIG. 2 has a single exhaust fan 128, the preferred embodiment includes a pair of exhaust fans 128 (FIG. 13) mounted to the rear wall thereof to provide cooling of the light source within the sanitizer.

Figure 13:
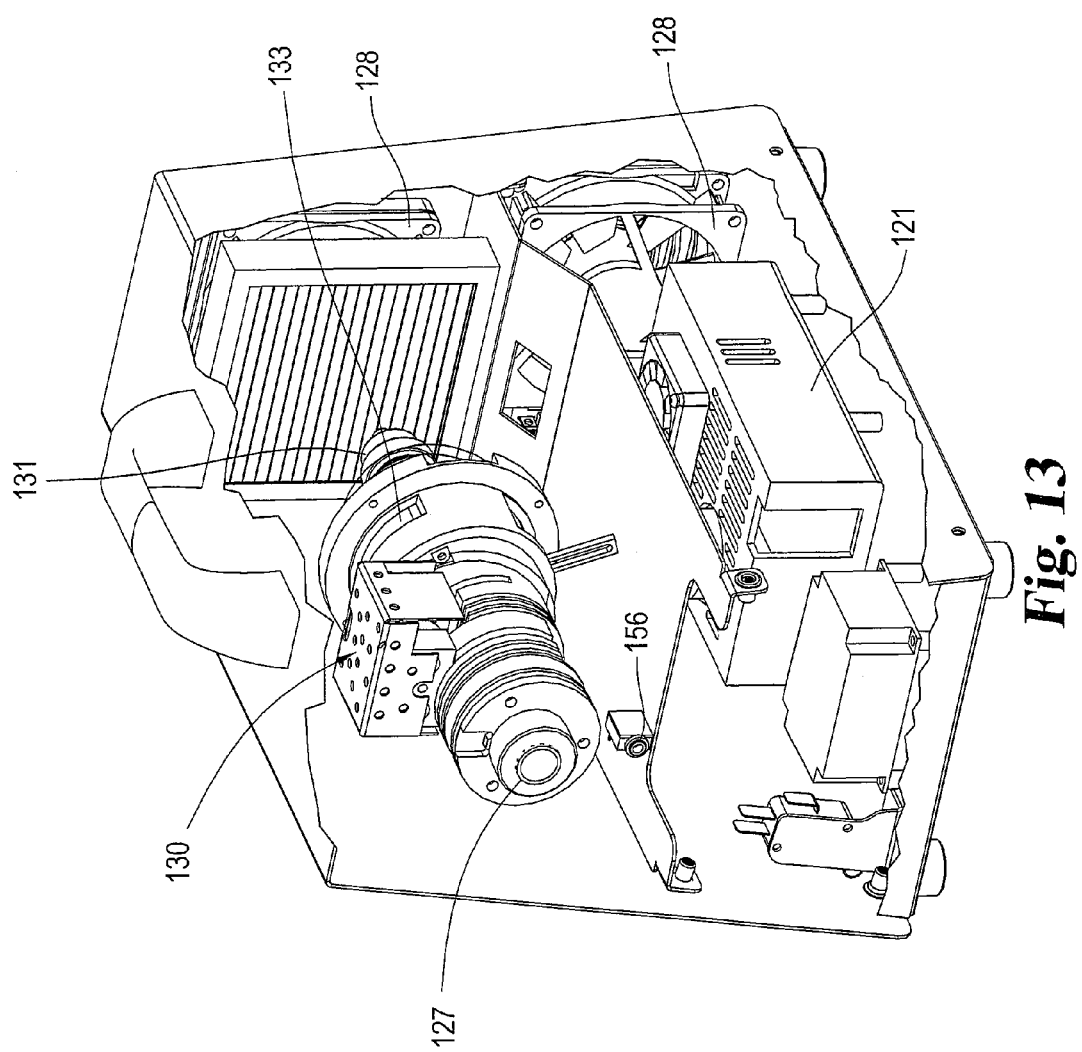
FIG. 13 is the same view as FIG. 12 only showing the outer housing fragmented illustrating the inner components.
Figure 22:
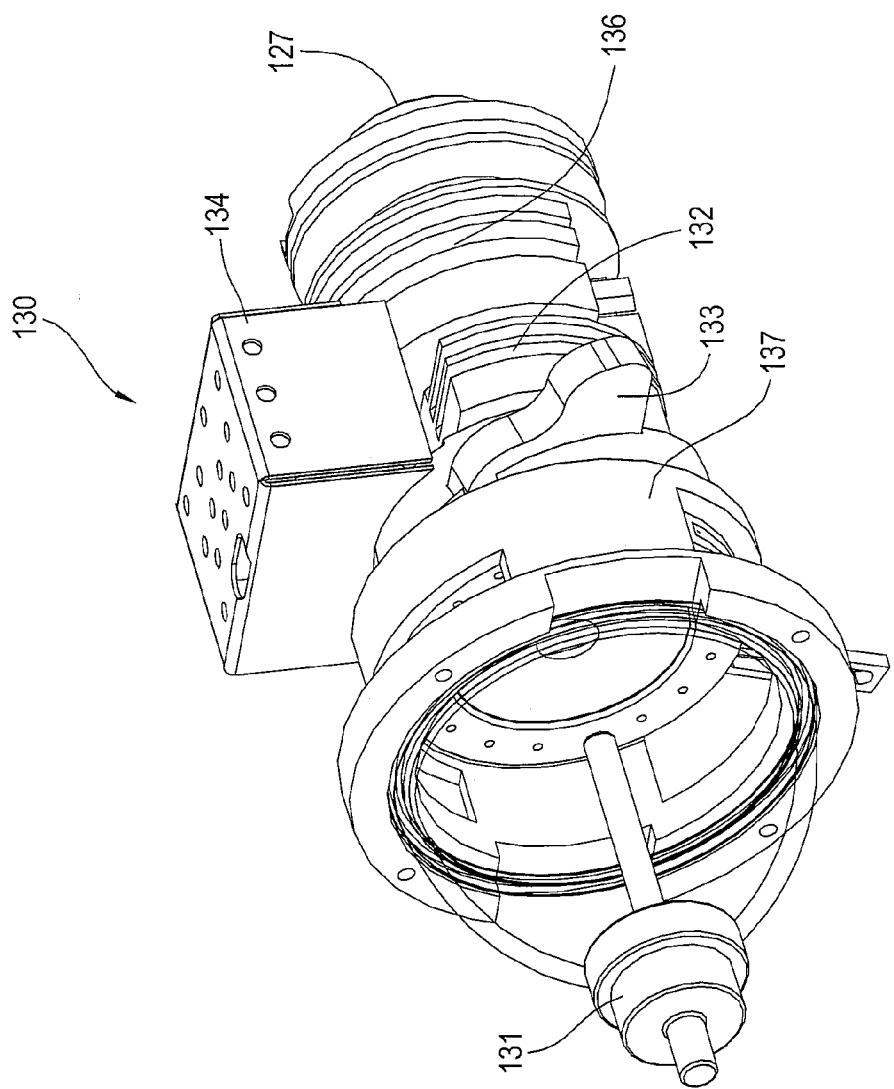
FIG. 22 is an enlarged perspective view of the lamp generator looking from lamp 131 (FIG. 13).

A conventional electric plug 180 (FIG. 11) connects the external source of electrical energy to the internal power supply 121 (FIG. 13) located within the sanitizer housing. Power supply 121 is connected to the light generator 130. The sanitizer housing is fragmented in FIG. 13 showing the conventional components of the preferred embodiment of the present invention. Power supply 121 is commercially available under Part No. E5b1055 from American Ultraviolet, 212 S. Mt. Zion Road, Lebanon, Ind. 46052. The power supply is connected to the light generator 130 (FIG. 22) which includes an arc lamp 131 consisting of a light source surrounded by a parabolic reflector, a shutter 132, a filter 133, a culminator 136, and an outlet 127. The arc lamp and parabolic reflector 131 is commercially available under Part Number LPB 1014 from American Ultraviolet. The combined bulb and reflector 131 is attached to housing unit 137, in turn, including a removable filter 133, and a culminator 136. Housing unit 137 with the filter and culminator are available from American Ultraviolet under Part No. SSM3055. Filter 133 is slidable into the hollow interior housing unit 137 to block long wave lengths of the radiation emitted by bulb and reflector 131. An electromagnet 138 (FIG. 23) is mounted to enclosure 134, in turn, mounted to housing 137. Electromagnet 138 is operable to move shutter 132 to block, or control the amount of radiation emitted by the lamp and reflector component 131. Filter 133 is slidably mounted to housing 137 and may be pulled outwardly for replacement. The light generator 130 is operable to emit radiation via outlet 127 and includes UVC type radiation.

Figure 15:
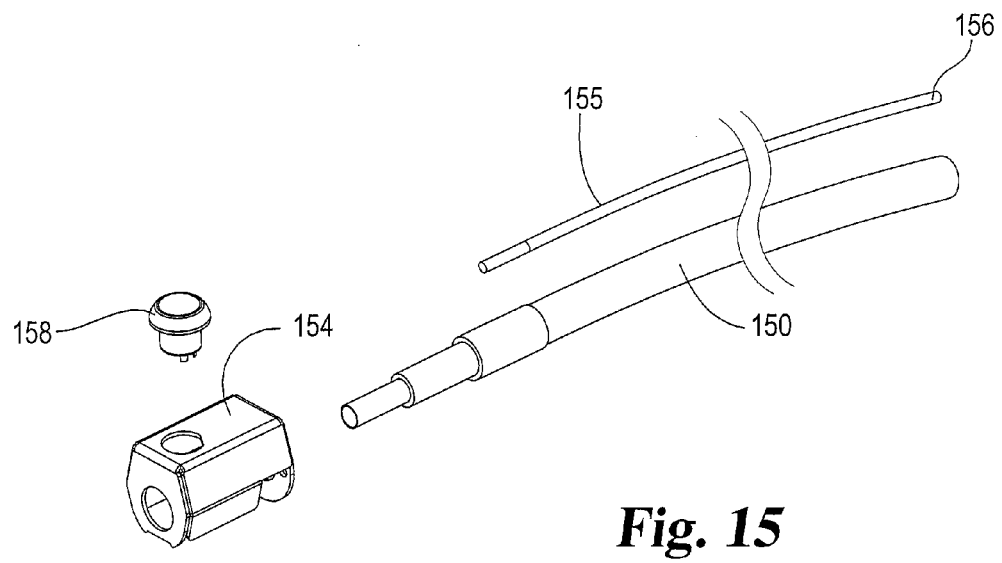
FIG. 15 is a fragmentary exploded view of the wand of FIG. 14.

Wand 150 (FIG. 14) has a flexible main body to transmit the UVC radiation from the source of radiation, namely generator 130 as filtered by infrared filter 133 toward the surface to be sanitized. The wand is shown as fragmented in FIGS. 14 and 15 since the main body of the wand is long and cannot be fully shown in the drawings. The main body of the wand has a proximal end 151 connected to the UVC outlet 127 (FIG. 12) via a commercially available connector. At the distal end of the wand main body is a push button switch 153 (FIG. 14) to control the flow of UVC radiation outwardly from the wand.

Figure 23:
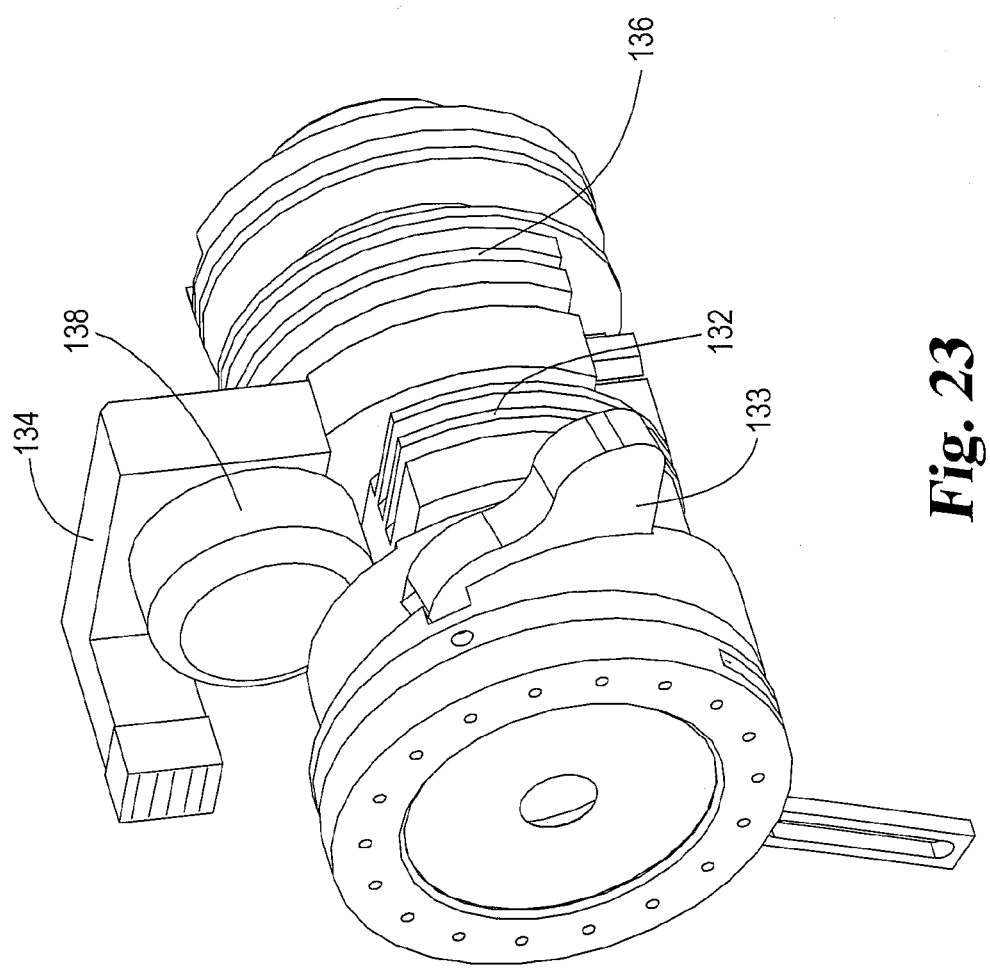
FIG. 23 is the same view as FIG. 22 only with the arc lamp removed therefrom.
Figure 24:
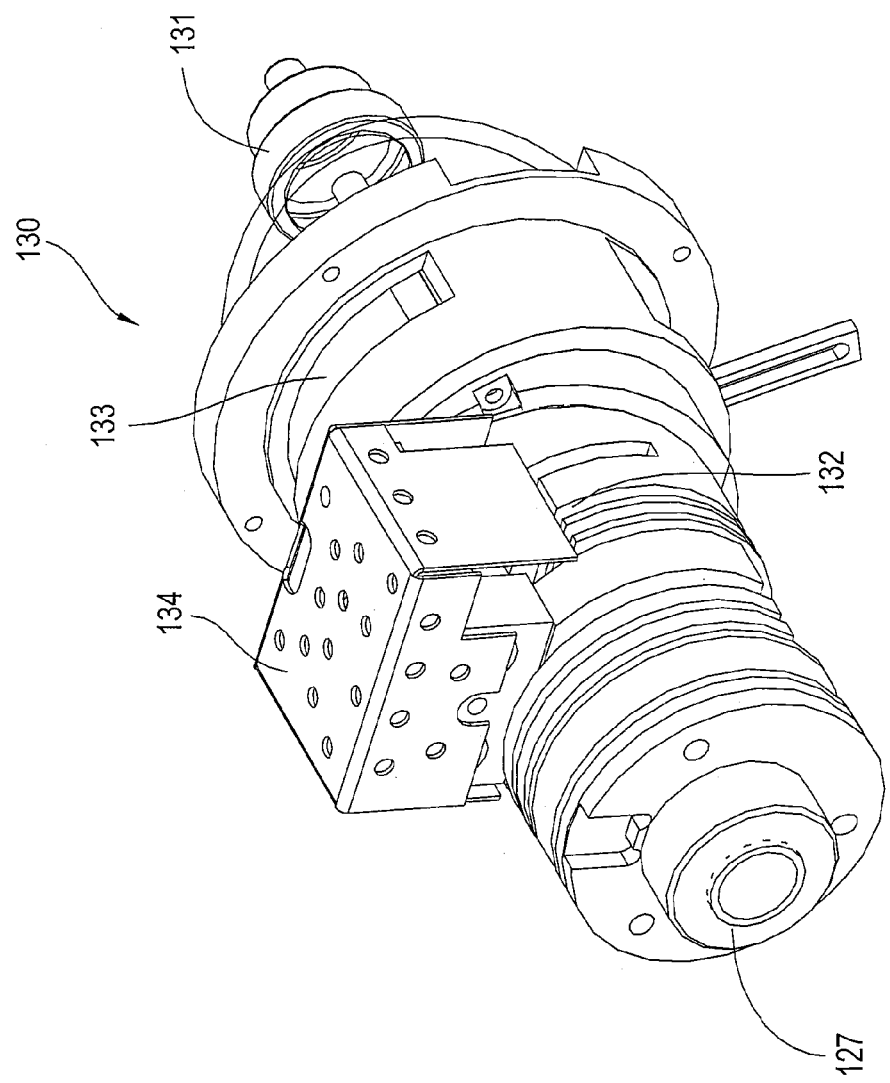
FIG. 24 is an enlarged perspective view of the light generator 130 shown in FIG. 13.

Switch 153 includes a switch housing 154 (FIG. 15) having a push button control 158 movably mounted thereon. Housing 154 is mounted to the distal end of wand 150 by conventional fastening devices. A switch wire 155 has one end operatively connected to the switch 153 with the opposite end of the switch wire 155 extending through portal 156 (FIG. 12), in turn, connected to the electro-magnet 138 (FIG. 23). The electro-magnet as previously discussed is operable to control the shutter 132 blocking or opening the passage from arc lamp 131 (FIG. 22) to the outlet 127. Thus, the user may grasp the distal end of the wand and direct the tip thereof towards the surface to be sanitized while activating or deactivating the flow of UVC radiation via operation of switch 153.

In the preferred embodiment of the sanitizer, the flexible light guide is available from different sources of supply as discussed for the alternate embodiment. Excellent results have been obtained by using the liquid light guide from Newport Corp., 150 Long Beach Road, Stratford, Conn. 06615 under Model No. 76843. The flexible light guide is enclosed in a flexible inter woven fabric loom available from TECH- FLEX, 29 Brookfield Dr., Sparta, N.J. 07871 under part number PTNO.63. The switch wire 155 may be secured to the main body of the flexible light guide by standard shrink wrap.

A variety of different types of tips are removably mountable to the distal end of the wand main body with each tip design to direct UVC radiation at a particular angle towards the surface to be sanitized.

Straight tip 180 is illustrated in FIG. 16 having an entrance aperture 181 to receive the distal end of the wand main body and a set screw to hold the wand to the tip. The UVC radiation then emits via outlet 182. In order to direct the UVC radiation at an angle, an angled tip 160 is provided and is identical in construction with straight tip 180 with the exception that the distal portion 166 of tip 160 is arranged at an obtuse angle relative to the proximal end portion 165 of the tip with the UVC radiation then exiting via outlet 164. In the case of straight tip 180, the main body of the tip has an inner portion and an outer portion which are parallel or extends along a straight line thereby directing UVC radiation directly outward along the straight line from the wand. A variation of angle tip 160 is a right angle or 90 degree tip 190 having an outer portion arranged at 90 degrees with respect to the inner portion of the tip thereby directing the UVC radiation at a right angle relative to the wand.

In the case of the tips shown in FIGS. 16-18, the main body of the tip is cylindrical in configuration. A spreader or fan tip 170 is illustrated in FIG. 19 wherein the outer cylindrical portion of the tip diverges thereby directing the radiation over an area larger than the diameter of the main body of the tip.

Figure 20:
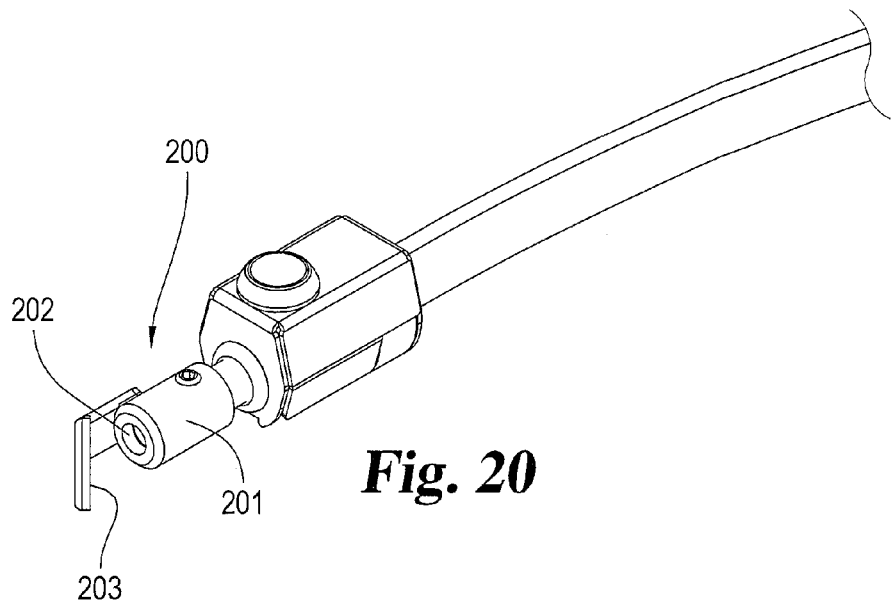
FIG. 20 is a perspective view of an angle reflector mounted to the wand distal end.
Figure 21:
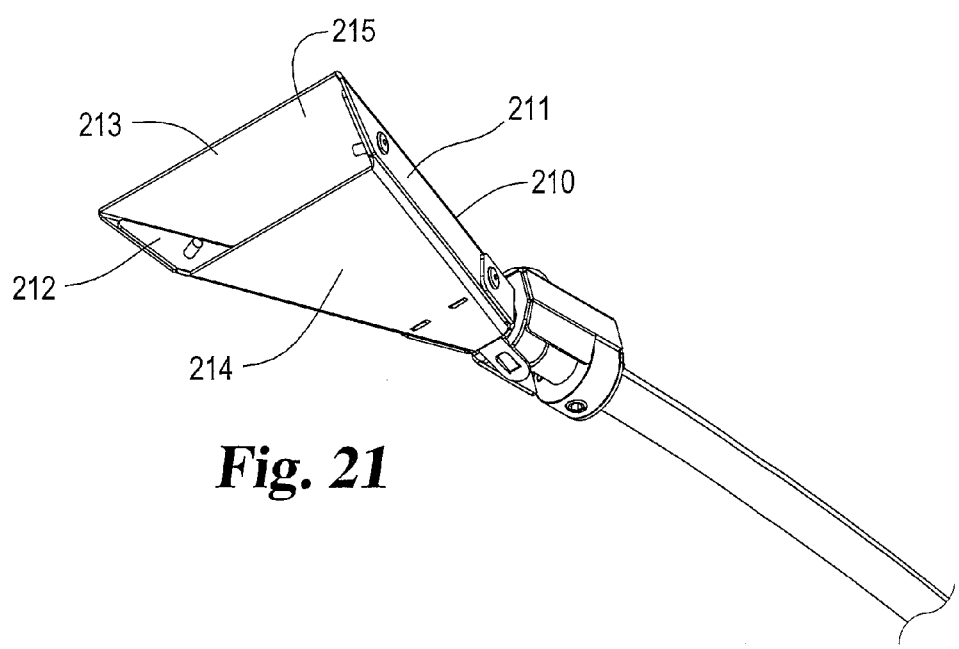
FIG. 21 is a perspective view of a reflector fan tip mounted to the wand distal end.

In lieu of allowing the radiation simply to exit the distal end of the particular tip utilized, a pair of reflector tips are shown in FIGS. 20 and 21. Reflector tip 200 includes a cylindrical portion 201 parallel with the distal end of the wand. The UFC radiation exits the reflector portion 201 via outlet 202 and is then reflected by a mirror type surface 203 arranged at obtuse angle relative to cylindrical portion 201. Reflector tip 210 has a pair of diverging side walls 211 and 212 joined to a diverging upper 213 wall and diverging lower wall 214 forming an expanding fan tip with the radiation exiting outlet 215 over a larger surface as compared to tips 160, 180 and 190.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An ultraviolet sanitizer with wand comprising:
a main housing;
an electrical power supply;
a fan mounted to said main housing and connected to said power supply operable to interiorly cool said main housing;
a generator connected to said power supply operable to generate ultraviolet radiation, type C, with a power output between 3.5 watts and 6.0 watts, said generator having an ultraviolet radiation emitting outlet; and,
a flexible wand having a main body to transmit ultraviolet radiation, said wand having a wand proximal end connected to said ultraviolet radiation emitting outlet of said generator to receive said ultraviolet radiation and a wand distal end to direct said ultraviolet radiation in the amount between 3.5 watts and 6.0 watts at said distal end against a surface to be sanitized; and wherein said generator includes a lamp, a movable shutter and an electromagnet to move said shutter, said shutter positioned between said radiation emitting outlet of said generator and said lamp, said wand distal end includes a manual switch thereon operatively connected to said electromagnet to move said shutter and control flow of ultraviolet radiation from said lamp to said radiation emitting outlet of said generator.

2. The sanitizer of claim 1 wherein:
said generator includes a reflector to focus radiation from said lamp.

3. The sanitizer of claim 2 wherein:
said generator includes a culminator located between said arc lamp and said outlet of said generator to focus radiation into a beam.

4. The sanitizer of claim 3 wherein:
said generator includes an infrared filter and an enclosure, said enclosure has said lamp, said reflector, said culminator, and said filter mounted therein, said enclosure is mounted within said main housing.

5. The sanitizer of claim 1 wherein and further comprising:
a radiation directing tip having a main body with a tip proximal end removably mountable on said wand distal end and a tip distal end to direct ultraviolet radiation against a surface to be sanitized, said main body extends from said tip proximal end to said tip distal end and includes a first portion located at said proximal end and a second flared portion located at said distal end spreading radiation against the surface being sanitized, said main body of said tip has a lower wall, a top wall and a pair of side walls joined together with said lower wall and said top wall diverging apart from said tip proximal end to said tip distal end and side walls diverging apart from said tip proximal end to said tip distal end forming an expanding fan tip.

6. The sanitizer of claim 1 wherein and further comprising:
a radiation reflecting tip having a main body with a tip proximal end removably mountable on said wand distal end and a tip distal end to direct by reflecting ultraviolet radiation against a surface to be sanitized, said main body extends from said tip proximal end to said tip distal end and includes a first portion located at said proximal end and a second portion located at said distal end reflecting radiation against the surface being sanitized, said main body has a cylindrical portion parallel with the distal end of the wand with the cylindrical portion having an outlet with a reflector portion with a mirror type surface arranged at an obtuse angle relative to said cylindrical portion.

7. The sanitizer of claim 1, further comprising:
a broad radiation directing tip having a much larger diameter than said flexible wand.

8. The sanitizer of claim 1, further comprising:
a reflector tip including:
    a coupling portion removable attachable to said flexible wand
    a flat mirror aligned with said flexible wand when said coupling portion is attached to said wand, wherein said flat mirror is arranged at an obtuse angle to said flexible wand.

9. The sanitizer of claim 1, further comprising:
a reflector tip including:
    a pair of diverging side walls;
    a diverging upper wall; and
    a diverging lower wall, wherein the diverging side walls, upper wall and lower wall form an expanding fan tip with an enlarged radiation exiting outlet.

10. The sanitizer of claim 1, further comprising a reflector coupled to said flexible wand, wherein said reflector is located distally from said wand radiation outlet.

11. A UV sanitizer with wand comprising:
an electrical power supply;
a generator of ultraviolet radiation, type C, with a power output between 3.5 watts and 6.0 watts, said generator having a generator radiation outlet with said generator including a lamp, a movable shutter and a mechanism to move said shutter;
a flexible wand having a flexible main body to transmit said radiation from said generator, said wand having a proximal end connected to said generator radiation outlet and a distal end forming a wand radiation outlet to direct said radiation in the amount between 3.5 watts and 6.0 watts against a surface to be sanitized; and,
a manual electrical switch mounted on said distal end of said wand, said shutter positioned relative to said lamp and wand radiation outlet to control flow of radiation from said lamp and through said wand radiation outlet, said switch connecting said mechanism to said power supply to move said shutter by said mechanism controlling flow of radiation out of said wand radiation outlet.

12. The UV sanitizer of claim 11 wherein said mechanism is an electro-magnet, said wand is a light guide for transmitting at 220 to 280 nanometers.

13. The UV sanitizer of claim 11 and further comprising a filter limiting passage of UV radiation to said wand radiation outlet; and, a parabolic reflector to focus radiation from said lamp.

14. The UV sanitizer of claim 13 and further comprising a culminator to focus radiation into a beam.

15. The UV sanitizer of claim 11 and further comprising a radiation tip mounted to said distal end of said wand, said tip having a lower wall, a top wall and a pair of side walls joined together with said lower wall and said top wall diverging apart from said distal end of said wand and side walls diverging apart from said distal end of said wand forming an expanding fan tip.

16. the UV sanitizer of claim 11, further comprising a reflector coupled to said flexible wand, wherein said reflector is located distally from said wand radiation outlet.

17. The sanitizer of claim 11, further comprising:
a broad radiation directing tip having a much larger diameter than said flexible wand.

18. The sanitizer of claim 11, further comprising:
a reflector tip including:
a coupling portion removable attachable to said flexible wand
a flat mirror aligned with said flexible wand when said coupling portion is attached to said wand, wherein said flat mirror is arranged at an obtuse angle to said flexible wand.

19. The sanitizer of claim 11, further comprising:
a reflector tip including:
a pair of diverging side walls;
a diverging upper wall; and
a diverging lower wall, wherein the diverging side walls, upper wall and lower wall form an expanding fan tip with an enlarged radiation exiting outlet.

* * * * *